United States Patent [19]

Schlosser et al.

[11] Patent Number: 5,820,785
[45] Date of Patent: Oct. 13, 1998

[54] FLUOROALKYLETHNYL- AND DIFLUOROALKYLETHYNYLBENZENES, AND THEIR USE IN LIQUID-CRYSTAL MIXTURES

[75] Inventors: Hubert Schlosser, Glashütten; Dietmar Jungbauer, Weiterstadt, both of Germany

[73] Assignee: Merck Patent Gesellschaft mit Beschrankter Haftung, Germany

[21] Appl. No.: 737,631

[22] PCT Filed: May 10, 1995

[86] PCT No.: PCT/EP95/01766

§ 371 Date: Nov. 18, 1996

§ 102(e) Date: Nov. 18, 1996

[87] PCT Pub. No.: WO95/32261

PCT Pub. Date: Nov. 30, 1995

[30] Foreign Application Priority Data

May 19, 1994 [DE] Germany .......................... 44 17 441.1

[51] Int. Cl.[6] .......................... C09K 19/30; C09K 19/34; C09K 19/12; C07C 19/08
[52] U.S. Cl. .................. 252/299.63; 252/299.6; 252/299.61; 252/299.62; 252/299.65; 252/299.66; 252/299.67; 560/100; 560/102; 560/108; 544/298; 546/339; 546/342; 570/128; 570/129; 570/144; 548/136
[58] Field of Search .......................... 252/299.63, 299.66, 252/299.6, 299.61, 299.62, 299.67, 299.65; 568/647; 585/25; 560/100, 102, 108; 570/128, 129, 144; 544/298, 335; 546/339, 342; 548/136; 349/183

[56] References Cited

U.S. PATENT DOCUMENTS

| | | | |
|---|---|---|---|
| 5,171,473 | 12/1992 | Buchecker et al. | 252/299.61 |
| 5,264,149 | 11/1993 | Buchecker et al. | 252/299.6 |
| 5,308,537 | 5/1994 | Coates et al. | 252/299.6 |
| 5,447,657 | 9/1995 | Schadt et al. | 252/299.01 |

*Primary Examiner*—C. H. Kelly
*Attorney, Agent, or Firm*—Millen, White, Zelano & Branigan, P.C.

[57] ABSTRACT

Disclosed are derivatives of fluoroalkylethynyl- and difluoroalkylethynylbenzenes of the formula (I) herein. These compounds exhibit useful properties as liquid crystal compounds and are useful in nematic liquid crystal mixtures.

21 Claims, No Drawings

FLUOROALKYLETHNYL- AND DIFLUOROALKYLETHYNYLBENZENES, AND THEIR USE IN LIQUID-CRYSTAL MIXTURES

The unusual combination of anisotropic and fluid behavior of liquid crystals has resulted in their use in electro-optical switching and display devices, where their electrical, magnetic, elastic and/or thermal properties can be utilized for changes in alignment. Optical effects can be achieved, for example, with the aid of birefringence, of the inclusion of dichroic dye molecules (guest host mode), or of light scattering.

The requirements of practice are constantly rising, not least also owing to the constantly increasing number of types of light valve (TN, STN, DSTN, TFT, ECB, DECB, DS, GH, PDLC, NCAP, SSFLC, DHF, SBF, etc.). Besides thermodynamic and electro-optical parameters, such as phase sequence and phase temperature range, refractive index, birefringence and dielectric anisotropy, response time, threshold voltage, steepness of the electro-optical characteristic line, elastic constants, electrical resistance, multiplexability or pitch and/or polarization in chiral phases, the stability of the liquid crystals to moisture, gases, temperature and electromagnetic radiation and to the materials with which they are in contact during and after the production process (for example alignment layers) is of considerable importance. Toxicological and ecological acceptability and price are constantly increasing in importance.

A broad review of the field of liquid crystals is offered, for example, by the literature below and the references cited therein:

H. Kelker, H. Hatz, Handbook of Liquid Crystals, Verlag Chemie, Weinheim, 1980;
W. E. De Jeu, Physical Properties of Liquid Crystal Materials, Gordon and Breach, Philadelphia, 1980;
H. Kresse, Dielectric Behaviour of Liquid Crystals, Fortschritte der Physik, Berlin 30, 10, 1982, 507–582;
B. Bahadur, Liquid Crystals: Applications and Uses, World Scientific, Singapore, 1990;
Landolt-Börnstein, New Series, Group IV, Volume 7 Liquid Crystals, 1992–1993 and
J. W. Goodby et al., Ferroelectric Liquid Crystals: Principles, Properties and Applications, Gordon Breach, Philadelphia, 1991.

WO 90/13610, EP 0 480 217 and DE-A-40 27 458 describe derivatives of trifluoromethylethynyl-, fluoroethynyl- and chloroethynylbenzene for use in liquid-crystal mixtures.

Since, however, individual compounds have hitherto been unable to satisfy simultaneously the many different requirements of liquid crystals, some of which are mentioned above, there is a constant demand for novel improved liquid-crystal mixtures and thus for a multiplicity of mesogenic and non-mesogenic compounds of different structure which enable the mixtures to be adapted to a very wide variety of applications. This applies both to the areas in which nematic LC phases are used in light valves and to those having smectic phases.

Surprisingly, it has now been found that derivatives of fluoroalkylethynyl- and difluoroalkylethynylbenzene are particularly suitable for use in nematic liquid-crystal mixtures.

The invention thus relates to novel fluoroalkylethynyl- and difluoroalkylethynylbenzenes of the general formula (I)

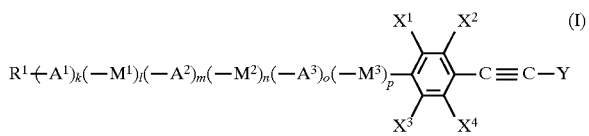

in which the symbols and indices have the following meanings:

$R^1$ is H, a straight-chain or branched (with or without an asymmetric carbon atom) alkyl group having 1 to 15 carbon atoms, in which, in addition, one or two non-adjacent $CH_2$ groups may be replaced by —O—, —S—, —CO—, —CO—O—, —O—CO—, —CO—S—, —S—CO—, —O—CO—O—, —CH=CH—, —C≡C—, cyclopropane-1,2-diyl or —Si(CH$_3$)$_2$—, and in which, in addition, one or more H atoms in the alkyl radical may be substituted by F, Cl or CN;

$A^1$, $A^2$ and $A^3$ are identical or different and are 1,4-phenylene, pyrazine-2,5-diyl, pyridine-2,5-diyl, pyrimidine-2,5-diyl, in which one or two H atoms may be replaced by F, trans-1,4-cyclohexylene, 1,3,4-thiadiazole-2,5-diyl, 1,3-dioxane-2,5-diyl, naphthalene-2,6-diyl, bicyclo [2.2.2]octane-1,4-diyl or 1,3-dioxoborinane-2,5-diyl;

$M^1$, $M^2$ and $M^3$ are identical or different and are —CH$_2$CH$_2$—, —CH=CH—, —C≡C—, —CH$_2$CH$_2$CH$_2$CH$_2$—, —CH$_2$CH$_2$CH$_2$—O—, —O—CH$_2$CH$_2$CH$_2$—, —CH$_2$CH$_2$—CO—O—, —O—CO—CH$_2$CH$_2$—, —CH$_2$—O—, —O—CH$_2$—, —CO—O— or —O—CO—;

k, l, m, n, o and p are zero or one, with the proviso that the sum k+m+o is greater than zero;

$X^1$, $X^2$, $X^3$ and $X^4$ are, independently of one another, H, F or Cl;

Y is a fluorinated alkyl radical having 1 to 3 carbon atoms.

The novel compounds of the general formula (I) are chemically and photochemically stable. They have low melting points and generally have broad liquid-crystalline phases, in particular broad nematic phases.

In particular, the novel compounds have very high anisotropy of the refractive index and of the dielectric constant, which makes them particularly suitable for use in TFT-TN and STN mixtures., In a preferred embodiment of the invention, the symbols and indices in the formula (I) have the following meanings:

$R^1$ is a straight-chain alkyl having 1 to 15 carbon atoms;

$A^1$, $A^2$ and $A^3$ are identical or different and are 1,4-phenylene, in which one or two H atoms may be replaced by F, or trans-1,4-cyclohexylene;

$M^1$, $M^2$ and $M^3$ are identical or different and are —CH$_2$CH$_2$—, —C≡C—, —CH$_2$CH$_2$CH$_2$CH$_2$—, —CH$_2$CH$_2$CH$_2$—O—, —O—CH$_2$CH$_2$CH$_2$—, —CH$_2$CH$_2$—CO—O—, —O—CO—CH$_2$CH$_2$—, —CH$_2$—O—, —O—CH$_2$—, —CO—O— or —O—CO—;

k, l, m, n, o and p are zero or one, with the proviso that the sum k+m+o is greater than zero;

$X^1$, $X^2_1$ $X^3$ and $X^4$ are, independently of one another, H or F; and

Y is preferably —CH$_2$F or —CHF$_2$.

Particularly preferred compounds of the formula (I) are the fluoroalkylethynyl- and difluoroalkylethynylbenzenes of the formulae (I1) to (I44) listed below:

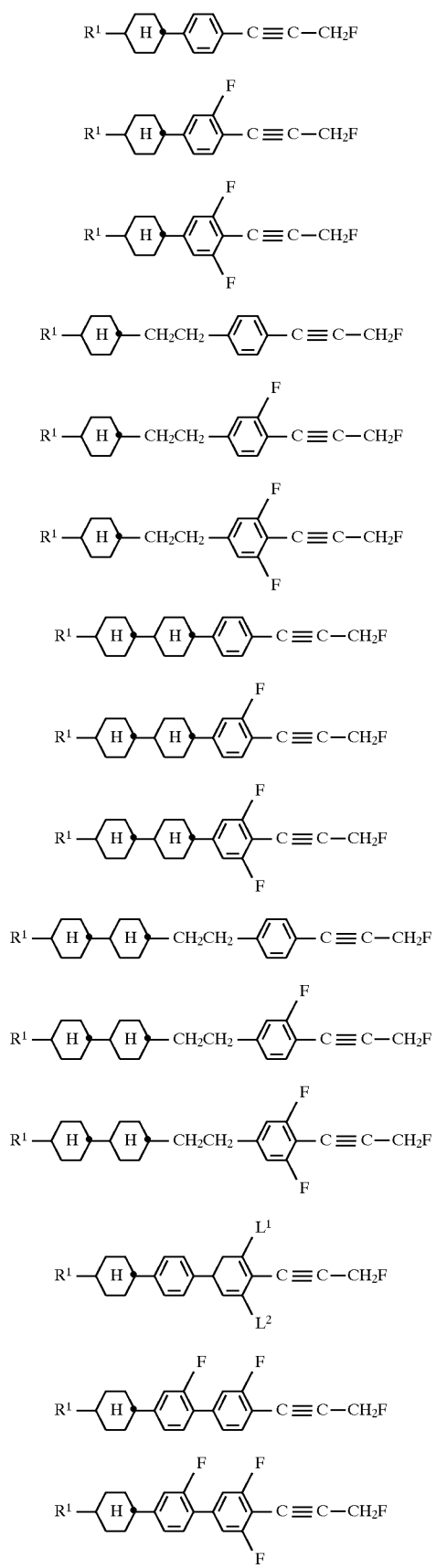
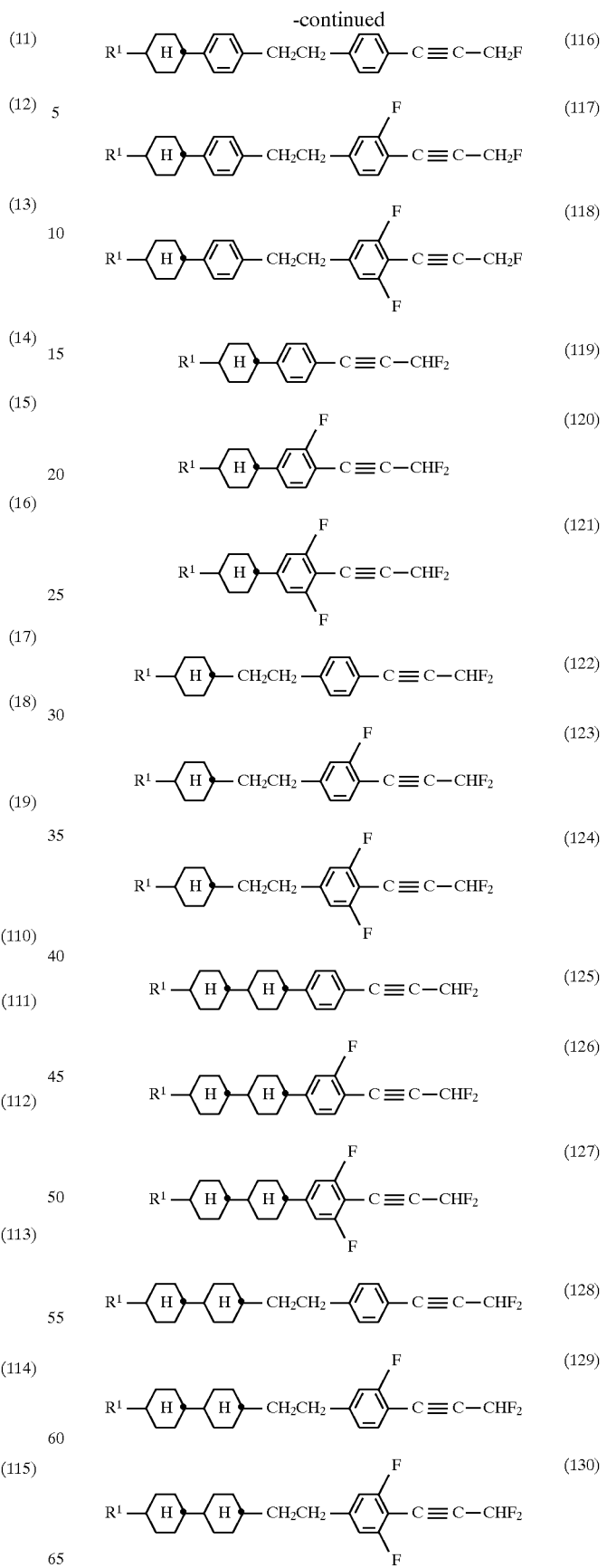

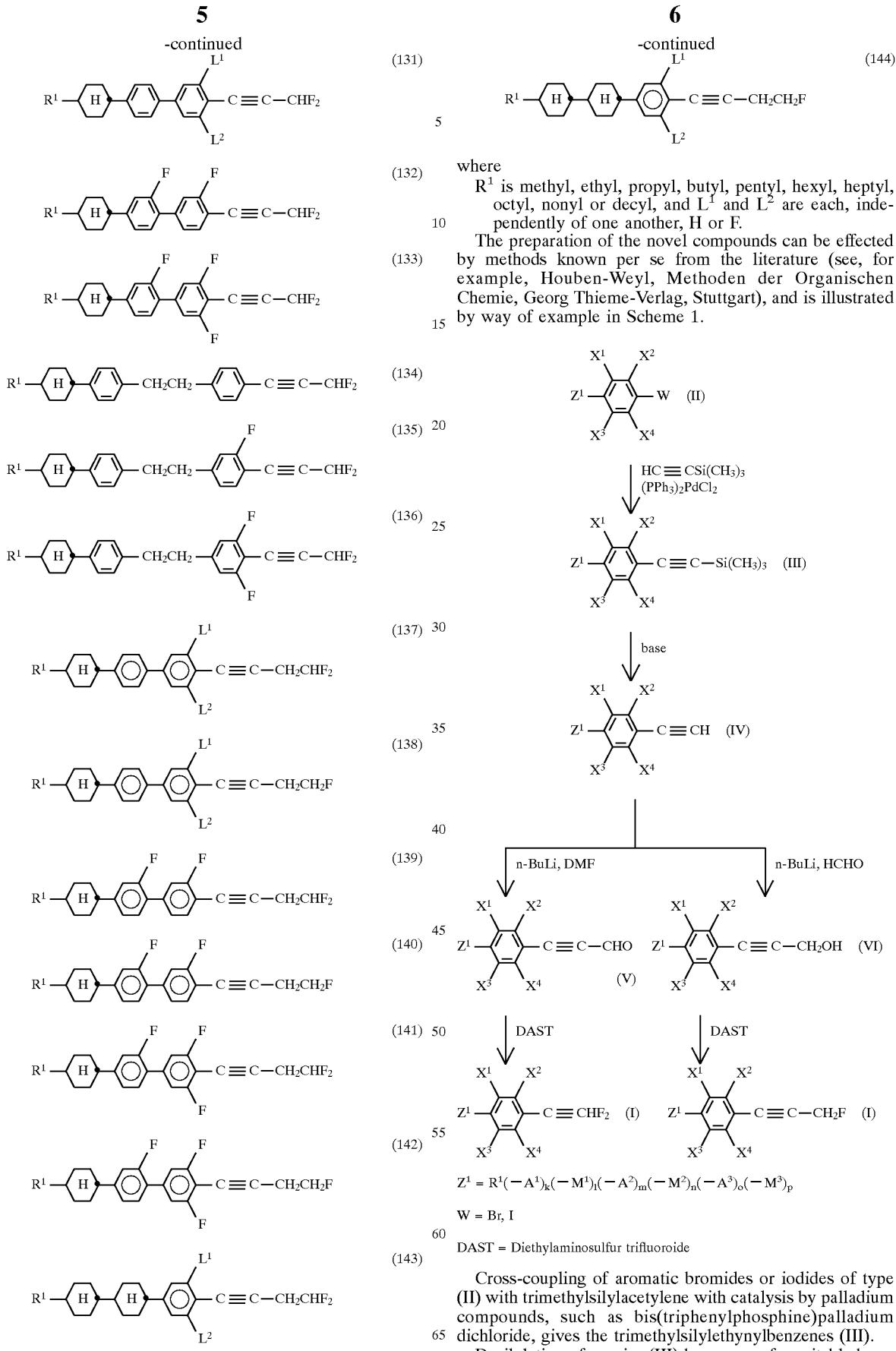

where
R[1] is methyl, ethyl, propyl, butyl, pentyl, hexyl, heptyl, octyl, nonyl or decyl, and L[1] and L[2] are each, independently of one another, H or F.

The preparation of the novel compounds can be effected by methods known per se from the literature (see, for example, Houben-Weyl, Methoden der Organischen Chemie, Georg Thieme-Verlag, Stuttgart), and is illustrated by way of example in Scheme 1.

$Z^1 = R^1(-A^1)_k(-M^1)_l(-A^2)_m(-M^2)_n(-A^3)_o(-M^3)_p$

W = Br, I

DAST = Diethylaminosulfur trifluoroide

Cross-coupling of aromatic bromides or iodides of type (II) with trimethylsilylacetylene with catalysis by palladium compounds, such as bis(triphenylphosphine)palladium dichloride, gives the trimethylsilylethynylbenzenes (III).

Desilylation of species (III) by means of a suitable base, for example potassium hydroxide, gives the ethynylbenzenes (IV), which, after deprotonation, for example using n-butyllithium, and reaction with the electrophiles dimethylformamide or formaldehyde, gives the formylethynylbenzenes (V) and the hydroxymethylethynylbenzenes (VI) (see in this respect: S. Takahashi, Y. Kuroyama, K. Sonogashira, N. Hagihara, Synthesis 1980, 627).

Reaction of the compounds of type (V) and (VI) with diethylaminosulfur trifluoride (DAST) gives the novel fluoromethylethynyl- and difluoromethylethynylbenzenes (I) (see in this respect: M. Hudlicky in Organic Reactions, Vol. 35, p. 513).

The above-described process is likewise a subject-matter of the invention.

The radical

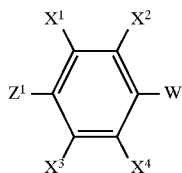

is synthesized by methods known per se and customary to the person skilled in the art.

This preparation is carried out under reaction conditions which are known and suitable for said reactions. One may also make use here of variants which are known per se but are not mentioned here in greater detail.

Reference may be made, for example, to DE-A 23 44 732, 24 50 088, 24 29 093, 25 02 94, 26 36 684, 27 01 591 and 27 52 975 for compounds containing 1,4-cyclohexylene and 1,4-phenylene groups; DE-A 26 41 724 for compounds containing pyrimidine- 2,5-diyl groups; DE-A 40 26 223 and EP-A 03 91 203 for compounds containing pyridine-2,5-diyl groups; DE-A 32 31 462 for compounds containing pyridazine-3,6-diyl groups, EP-A 309 514 for compounds containing 1,3,4-thiadiazole-2,5-diyl groups, WO 92/16500 for naphthalene-2,6-diyl groups; DE 3710-890 for bicyclo[2.2.2]octane-1,4-diyl groups; K. Seto, H. Matsubara, S. Takahashi, T. Takara, M. Murakami, S. Miyake, T. Masumi, T. Ando, A. Fukami, Journal of the Chemical Society, Chemical Communications, 1988, 56, for dioxoborinane-2,5-diyl groups.

The preparation of disubstituted pyridines, disubstituted pyrazines and disubstituted pyrimidines is also given, for example, in the corresponding volumes of the series "The Chemistry of Heterocyclic Compounds" by A. Weissberger and E. C. Taylor (editors).

Dioxane derivatives are expediently prepared by reaction of an appropriate aldehyde (or a reactive derivative thereof) with an appropriate 1,3-diol (or a reactive derivative thereof), preferably in the presence of an inert solvent, such as benzene or toluene, and/or in the presence of a catalyst, for example a strong acid, such as sulfuric acid or benzene- or p-toluenesulfonic acid, at temperatures between about 20° C. and about 150° C., preferably between 80° C. and 120° C. Suitable reactive derivatives of the starting materials are primarily acetals.

Some of said aldehydes and 1,3-diols and reactive derivatives thereof are known, and some can be prepared without difficulties from compounds known from the literature by standard methods of organic chemistry. For example, the aldehydes are obtainable by oxidation of corresponding alcohols or by reduction of nitriles or corresponding carboxylic acids or derivatives thereof, and the diols by reduction of corresponding diesters.

Compounds in which an aromatic ring carries at least one F atom as substituent can also be obtained from the corresponding diazonium salts by replacement of the diazonium group by a fluorine atom, for example by the Baltz and Schiemann methods.

Regarding linking of the ring systems to one another, reference is made to: N. Miyaura, T. Yanagai and A. Suzuki, Synthetic Communications 1981, 11, 513–519; DE-C-39 30 663, M. J. Sharp, W. Cheng, V. Snieckus Tetrahedron Letters 1987, 28, 5093; G. W. Gray, J. Chem. Soc. Perkin Trans II 1989, 2041 and Mol. Cryst. Liq. Cryst. 1989, 172, 165; 1991, 204, 43 and 91; EP-A 0 449 015; WO 89/12039; WO 89/03821 and EP-A 0 354 4 34 for the direct linking of aromatics and heteroaromatics; DE-A 32 01 721 for compounds containing —CH$_2$CH$_2$— bridges, and Koji Seto et al., Liquid Crystals 1990, 8, 861–870, for compounds containing —C≡C— bridges.

Esters of the formula (I) can also be obtained by esterification of corresponding carboxylic acids (or reactive derivatives thereof) using alcohols or phenols (or reactive derivatives thereof) or by the DCC method (DCC=dicyclohexylcarbodiimide).

The corresponding carboxylic acids and alcohols or phenols are known and can be prepared analogously to known processes.

Particularly suitable reactive derivatives of said carboxylic acids are the acid halides, especially the chlorides and bromides, and furthermore the anhydrides, for example also mixed anhydrides, azides or esters, in particular alkyl esters having 1 to 4 carbon atoms in the alkyl group.

Suitable reactive derivatives of said alcohols and phenols are, in particular, the corresponding metal alkoxides and phenoxides, preferably of an alkali metal, such as sodium or potassium.

The esterification is advantageously carried out in the presence of an inert solvent. Particularly suitable solvents are ethers, such as diethyl ether, di-n-butyl ether, THF, dioxane or anisole, ketones, such as acetone, butanone or cyclohexanone, amides, such as DMF or hexamethylphosphoric triamide, hydrocarbons, such as benzene, toluene or xylene, halogenated hydrocarbons, such as tetrachloromethane, dichloromethane or tetrachloroethylene, and sulfoxides, such as dimethyl sulfoxide or sulfolane.

Ethers of the formula (I) are obtainable by etherification of corresponding hydroxyl compounds, preferably corresponding phenols, where the hydroxyl compound is expediently first converted into a corresponding metal derivative, for example into the corresponding alkali metal alkoxide or alkali metal phenoxide by treatment with NaH, NaNH$_2$, NaOH, KOH, Na$_2$CO$_3$ or K$_2$CO$_3$. This can then be reacted with the corresponding alkyl halide, sulfonate or dialkyl sulfate, expediently in an inert solvent, such as acetone, 1,2-dimethoxyethane, DMF or dimethyl sulfoxide, or alternatively with an excess of aqueous or aqueous-alcoholic NaOH or KOH at temperatures between about 20° C. and 100° C.

Regarding the synthesis of specific radicals R$^1$, reference may additionally be made, for example, to EP-A 0 355 008 for compounds having silicon-containing side chains, and EP-A 0 292 954 and EP-A 0 398 155 for compounds with cyclopropyl groups in the side chain.

The provision of compounds of the formula (I) very generally considerably broadens the range of liquid-crystalline substances which are suitable, from various applicational standpoints, for the preparation of liquid-crystalline mixtures.

The compounds of the formula (I) have a broad range of applications. Depending on the choice of substituents, these compounds can be used as base materials from which liquid-crystalline phases are predominantly composed; or, however, compounds of the formula (I) can be added to liquid-crystalline base materials from other classes of compound in order, for example, to modify the dielectric and/or optical anistropy of a dielectric of this type and/or to optimize its threshold voltage and/or its viscosity.

In the pure state, the compounds of the formula (I) are colorless and form liquid-crystalline mesophases in a temperature range which is favorably located for electro-optical use. They are stable chemically, thermally and with respect to light.

Compounds of the formula (I) can be used for the preparation of nematic or alternatively chirally nematic liquid-crystal mixtures, which are suitable for use in electro-optical or fully optical elements, for example display elements, switching elements, light modulators, elements for image processing, signal processing or generally in the area of nonlinear optics.

The invention therefore also relates to the use of compounds of the formula (I) in liquid-crystal mixtures, in particular nematic and chirally nematic liquid-crystal mixtures.

The invention also relates to liquid-crystal mixtures comprising one or more compounds of the formula (I).

The novel liquid-crystal mixtures generally consist of from 2 to 20, preferably from 2 to 15, components, including at least one, preferably from 1 to 5, particularly preferably from 1 to 3, compounds of the formula (I). The novel LC mixtures can be, for example, nematic or chirally nematic. The novel liquid-crystal mixtures generally comprise from 0.1 to 70 mol %, preferably from 0.5 to 50 mol %, in particular from 1 to 25 mol %, of the novel fluoromethylethynyl- and difluoromethylethynylbenzene derivatives of the formula (I). Further constituents of the novel mixtures are preferably selected from known compounds having nematic or cholesteric phases, including, for example, biphenyls, terphenyls, phenylcyclohexanes, bicyclohexanes, cyclohexylbiphenyls, and mono-, di- and trifluorophenyls. In general, commercially available liquid-crystal mixtures, even before addition of the novel compound(s), are mixtures of various components, of which at least one is mesogenic.

Suitable further constituents of novel nematic or chirally nematic liquid-crystal mixtures are, for example, 4-fluorobenzenes, as described, for example, in EP-A 494 368, WO 92/06 148, EP-A 460 436, DE-A 41 11 766, DE-A 41 12 024, DE-A 41 12 001, DE-A 41 00 288, DE-A 41 01 468, EP-A 423 520, DE-A 392 3064, EP-A 406 468, EP-A 393 577, EP-A 393 490, 3,4-difluorobenzenes, as described, for example, in DE-A 41 08 448, EP-A 507 094 and EP-A 502 407, 3,4,5-trifluorobenzenes, as described, for example, in DE-A 41 08 448 and EP-A 387 032, 4-benzotrifluorides, as described, for example, in DE-A 41 08 448, and phenylcyclohexanes, as described, for example, in DE-A 41 08 448.

The novel liquid-crystal mixtures are prepared in a manner which is conventional per se. In general, the components are dissolved in one another, preferably at elevated temperature.

Liquid-crystal mixtures which comprise compounds of the general formula (I) are particularly suitable for use in electro-optical switching and display devices (displays). These displays are usually constructed in such a way that a liquid-crystal layer is surrounded on both sides by layers which are usually, in this sequence starting from the LC layer, at least one alignment layer, electrodes and a limiting plate (for example made of glass). In addition, they contain spacers, adhesive frames, polarizers and, for color displays, thin colored filter layers. Other possible components are anti-reflection, passivation, equalization and barrier layers and electrically nonlinear elements, such as thin-film transistors (TFTs) and metal-insulator-metal (MIM) elements. The structure of liquid-crystal displays has already been described in detail in relevant monographs (for example E. Kaneko, "Liquid Crystal TV Displays: Principles and Applications of Liquid Crystal Displays", KTK Scientific Publishers, 1987, pages 12–30 and 63–172).

The novel liquid-crystal mixtures are particularly suitably for use in STN (super twisted nematics) and TFT-TN (thin film transistor-twisted nematics) displays. Such display types are known and described, for example, in B. Bahadur (Ed.), Liquid Crystals, Applications and Uses (Vol. 1), World Scientific, Singapore, 1990, in Chapters 10, p. 231–274 (STN), and 15, p. 397–436 (TFT-TN).

The invention is described in greater detail by the examples without the desire for it to be limited thereby.

EXAMPLES

Various measurement methods are used for physical characterization of the novel compounds.

The phase transition temperatures are determined with the aid of a polarizing microscope from the changes in structure on heating. By contrast, the melting point is determined using a DSC instrument. The phase transition temperatures between the phases Isotropic (I)
Nematic (N or N*)
Smectic C ($S_C$ or $S_C$*)
Smectic A ($S_A$ or $S_A$*)
Crystalline (X)
Glass transition (Tg)

are given in °C., and the values are between the phase designations in the phase sequence.

If the values for heating and cooling are different, the latter are placed in parentheses, or the phase sequence is given with rising or falling temperature.

Electro-optical investigations are carried out by methods known from the literature (for example B. Bahadur: Liquid Crystals Application and Uses, Vol. 1, World Scientific, Singapore, 1990).

For nematic liquid crystals (pure or mixtures), the values for the optical and dielectric anisotropy and for the electro-optical characteristic line are recorded at a temperature of 25° C.

Liquid crystals which do not have a nematic phase at 25° C. are mixed to the extent of 10% by weight with ZLI-1565 and/or to the extent of 20% by weight with ZLI-4792 (commercial nematic liquid-crystal mixtures from E. Merck, Darmstadt), and the values are extrapolated from the results for the mixture.

Electro-optical characteristic lines are determined from the transmission of a measurement cell. To this end, the cell is positioned between crossed polarizers in front of a light source. A light detector whose sensitivity is optimized to the visible region of the light by means of filters is positioned behind the cell. The change in transmission is recorded analogously to the stepwise increase in the voltage applied to the cell. Parameters such as threshold voltage and steepness are determined therefrom.

The optical anistropy is determined using an Abbe refractometer (Zeiss). In order to align the liquid crystal, an alignment layer obtained from a 1% by weight lecithin/methanol solution is applied to the prism.

In order to determine the dielectric anisotropy, a measurement cell having homeotropic and planar alignment is in each case constructed and their capacitances and dissipation factors determined using a multifrequency LCR meter (Hewlett Packard 4274 A). The dielectric constants are calculated as described in the literature (W. Maier, G. Meier, Z. Naturforsch, 1961, 16a, 262 and W. H. de Jeu, F. Leenhonts, J. Physique 1978, 39, 869). The electrical parameter HR (holding ratio) is determined as described in the literature (M. Schadt, Linear and nonlinear liquid crystal materials, Liquid Crystals 1993, 14, 73–104).

In order to determine the response speed (τ) and contrast (C), the measurement cell is clamped on the rotating stage of a polarizing microscope between crossed analyzer and polarizer. For determination of the contrast, the measurement cell is positioned by rotation so that a photodiode displays minimal light transmission (dark state). The microscope illumination is adjusted so that the photodiode indicates the same light intensity for all cells. After a switching operation, the light intensity changes (bright state), and the contrast is calculated from the ratio between the light intensities in these states.

Example 1

1-(Fluoromethylethynyl)-4-(trans-4-pentylcyclohexyl)benzene:

10.00 g (32.36 mmol) of 1-bromo-4-(trans-4-pentylcyclohexyl)benzene, 3.89 g (35.60 mmol) of trimethylsilylacetylene, 0.45 g (0.65 mmol) of bis(triphenylphosphine)palladium(II) chloride and 0.062 g (0.32 mmol) of copper(I) iodide are heated for 6 hours at the reflux temperature in 100 ml of diisopropylamine. The solvent is subsequently stripped off, and the soluble constituents of the residue are chromatographed on silica gel using n-hexane, giving 7.32 g of 1-(trimethylsilylethynyl)-4-(trans-4-pentylcyclohexyl)benzene,

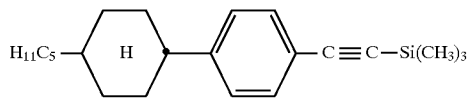

which is stirred for 1 hour at room temperature in 220 ml of methanol with 1.38 g (24.70 mmol) of potassium hydroxide. Work-up by evaporation of the solvent, partitioning between ether and water, drying and evaporation of the organic phase gives 4.95 g of 1-ethynyl-4-(trans-4-pentylcyclohexyl)benzene.

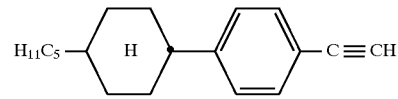

6.75 ml (10.80 mmol) of 1.6 molar n-butyllithium solution in n-hexane are added dropwise at 0° C. to 2.48 g of 1-ethynyl-4-(trans-4-pentylcyclohexyl)benzene in 25 ml of tetrahydrofuran. After 1 hour, this solution is saturated with formaldehyde, acidified by means of aqueous hydrochloric acid and partitioned between ether and water, and the organic phase is dried and evaporated. Chromatography on silica gel using n-hexane/dichloromethane (1:2) gives 1.80 g of 1-(hydroxymethylethynyl)-4-(trans-4-pentylcyclohexyl)benzene,

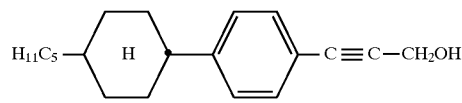

which is stirred for 2 hours at room temperature with 1.05 g (6.49 mmol) of diethylaminosulfur trifluoride in 10 ml of dichloromethane. After partitioning between water and dichloromethane, the organic phase is dried over sodium sulfate, evaporated and chromatographed on silica gel using n-heptane, giving 0.94 g of 1-(fluoromethylethynyl)-4-(trans-4-pentylcyclohexyl)benzene.

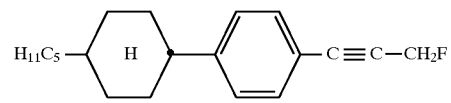

Examples 2 to 18 shown in Table 1 are prepared analogously to Example 1:

Table 1: Examples 2 to 30

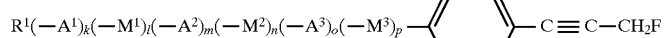

| Example No. | |
|---|---|
| 2 | 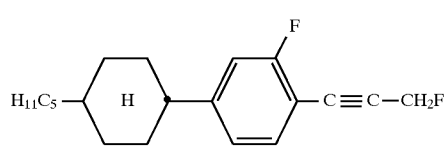 |

-continued

| | $R^1(-A^1)_k(-M^1)_l(-A^2)_m(-M^2)_n(-A^3)_o(-M^3)_p$ — [phenyl with $X^1, X^2, X^3, X^4$] — C≡C—CH$_2$F |
|---|---|
| Example No. | |

3: H$_{11}$C$_5$—[Cy(H)]—[Ph(2,5-diF)]—C≡C—CH$_2$F

4: H$_{11}$C$_5$—[Cy(H)]—CH$_2$CH$_2$—[Ph]—C≡C—CH$_2$F

5: H$_{11}$C$_5$—[Cy(H)]—CH$_2$CH$_2$—[Ph(2-F)]—C≡C—CH$_2$F

6: H$_{11}$C$_5$—[Cy(H)]—CH$_2$CH$_2$—[Ph(2,6-diF)]—C≡C—CH$_2$F

7: H$_7$C$_3$—[Cy(H)]—[Cy(H)]—[Ph]—C≡C—CH$_2$F

8: H$_9$C$_4$—[Cy(H)]—[Cy(H)]—[Ph(2-F)]—C≡C—CH$_2$F

9: H$_{11}$C$_5$—[Cy(H)]—[Cy(H)]—[Ph(2,6-diF)]—C≡C—CH$_2$F

10: H$_{11}$C$_5$—[Cy(H)]—[Cy(H)]—CH$_2$CH$_2$—[Ph]—C≡C—CH$_2$F

11: H$_7$C$_3$—[Cy(H)]—[Cy(H)]—CH$_2$CH$_2$—[Ph(2-F)]—C≡C—CH$_2$F

12: H$_{11}$C$_5$—[Cy(H)]—[Cy(H)]—CH$_2$CH$_2$—[Ph(2,6-diF)]—C≡C—CH$_2$F

-continued
| Example No. | $R^1(-A^1)_k(-M^1)_l(-A^2)_m(-M^2)_n(-A^3)_o(-M^3)_p$ — [phenyl with $X^1, X^2, X^3, X^4$] — C≡C—CH$_2$F |
|---|---|
| 13 | 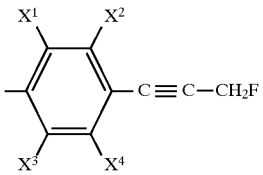 Phase sequence: X 171 S$_A$ 223 N 229 I |
| 14 | 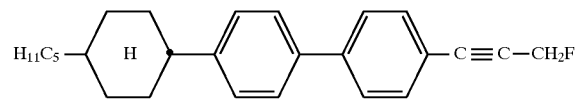 |
| 15 | 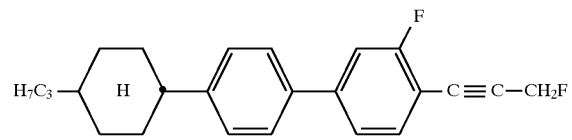 |
| 16 | 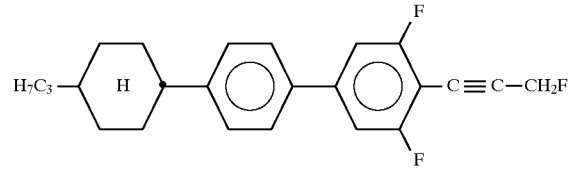 |
| 17 | 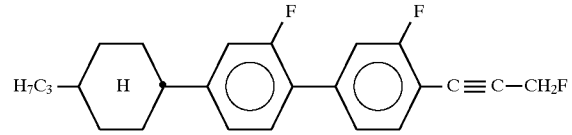 |
| 18 | 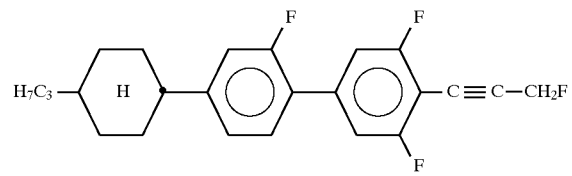 |
| 19 | 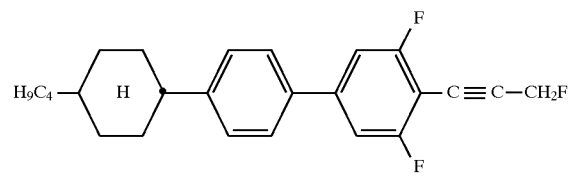 |
| 20 | 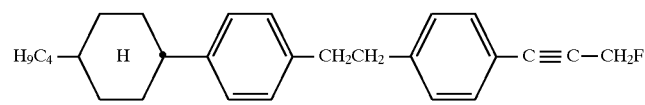 |
| 21 | 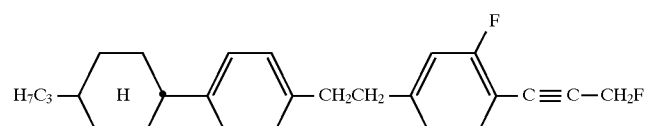 |

-continued $$R^1(-A^1)_k(-M^1)_l(-A^2)_m(-M^2)_n(-A^3)_o(-M^3)_p-\begin{matrix}X^1 & X^2\\ &\\ X^3 & X^4\end{matrix}-C\equiv C-CH_2F$$

| Example No. | Structure |
|---|---|
| 22 | $H_{11}C_5$—[H]—[H]—[Ph]—C≡C—CH$_2$CH$_2$F |
| 23 | $H_{11}C_5$—[H]—[H]—[Ph(3-F)]—C≡C—CH$_2$CH$_2$F |
| 24 | $H_{11}C_5$—[H]—[H]—[Ph(3,5-F$_2$)]—C≡C—CH$_2$CH$_2$F |
| 25 | $H_{11}C_5$—[H]—[Ph]—[Ph]—C≡C—CH$_2$CH$_2$F |
| 26 | $H_{11}C_5$—[H]—[Ph]—[Ph(3-F)]—C≡C—CH$_2$CH$_2$F |
| 27 | $H_{11}C_5$—[H]—[Ph]—[Ph(3,5-F$_2$)]—C≡C—CH$_2$CH$_2$F |
| 28 | $H_{11}C_5$—[H]—[Ph(2-F)]—[Ph(3-F)]—C≡C—CH$_2$CH$_2$F |
| 29 | $H_{11}C_5$—[H]—[Ph(2-F)]—[Ph(3,5-F$_2$)]—C≡C—CH$_2$CH$_2$F |
| 30 | $H_{11}C_5$—[H]—[Ph(2,6-F$_2$)]—[Ph(3-F)]—C≡C—CH$_2$CH$_2$F |

Example 31

1-(Difluoromethylethynyl)-4-(trans-4-pentylcyclohexyl)benzene 6.75 ml (0.80 mmol) of 1.6 molar n-butyllithium solution in n-hexane are added dropwise at 0° C. to 2.48 g (9.80 mmol) of 1-ethynyl-4-(trans-4-pentylcyclohexyl)benzene in 25 ml of tetrahydrofuran. After 1 hour, this solution is added dropwise to 0.83 ml of dimethylformamide in 20 ml of tetrahydrofuran, the mixture is stirred at room temperature for 1 hour, acidifed by means of aqueous hydrochloric acid and partitioned between ether and water, and the organic phase is dried and evaporated. Chromatography on silica gel using n-hexane/dichloromethane (1:1) gives 1.75 g of 1-(formylethynyl)-4-(trans-4-pentylcyclohexyl)benzene,

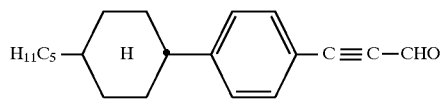

which is stirred for 2 hours at room temperature with 1.05 g (6.49 mmol) of diethylaminosulfur trifluoride in 10 ml of dichloromethane. After partitioning between water and dichloromethane, the organic phase is dried over sodium sulfate, evaporated and chromatographed on silica gel using n-heptane, giving 0.89 g of product

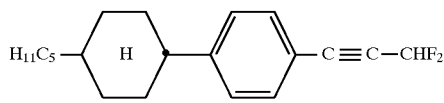

having the phase sequence

X 37 (26) N (34) I.

Examples 32 to 59 shown in Table 2 are prepared analogously to Example 31:

TABLE 2

Examples 32 to 59

$$R^1(-A^1)_k(-M^1)_l(-A^2)_m(-M^2)_n(-A^3)_o(-M^3)_p-\underset{X^3\ X^4}{\overset{X^1\ X^2}{\bigcirc}}-C\equiv C-CHF_2$$

| Example No. | Structure |
|---|---|
| 32 | H₁₁C₅—⟨H⟩—⟨⟩(F)—C≡C—CHF₂ |
| 33 | H₇C₃—⟨H⟩—⟨⟩(F,F)—C≡C—CHF₂ |
| 34 | H₉C₄—⟨H⟩—CH₂CH₂—⟨⟩—C≡C—CHF₂ |
| 35 | H₁₁C₅—⟨H⟩—CH₂CH₂—⟨⟩(F)—C≡C—CHF₂ |
| 36 | H₁₁C₅—⟨H⟩—CH₂CH₂—⟨⟩(F,F)—C≡C—CHF₂ |

TABLE 2-continued
Examples 32 to 59
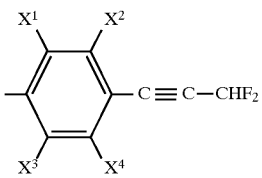
| Example No. | Structure |
|---|---|
| 37 | H₉C₄—[H]—[H]—[Ph]—C≡C—CHF₂ |
| 38 | H₇C₃—[H]—[H]—[Ph-F]—C≡C—CHF₂ |
| 39 | H₁₁C₅—[H]—[H]—[Ph-F,F]—C≡C—CHF₂ |
| 40 | H₁₁C₅—[H]—[H]—CH₂CH₂—[Ph]—C≡C—CHF₂ |
| 41 | H₁₁C₅—[H]—[H]—CH₂CH₂—[Ph-F]—C≡C—CHF₂ |
| 42 | H₉C₄—[H]—[H]—CH₂CH₂—[Ph-F,F]—C≡C—CHF₂ |
| 43 | H₁₁C₅—[H]—[Ph]—[Ph]—C≡C—CHF₂ |
Phase sequence: X 114 (55) S$_X$ 166 S$_A$ 204 N 217 I
| 44 | H₁₁C₅—[H]—[Ph]—[Ph-F]—C≡C—CHF₂ |
|---|---|
| 45 | H₁₁C₅—[H]—[Ph]—[Ph-F,F]—C≡C—CHF₂ |
Phase sequence: X 87 (52) N 164 I TABLE 2-continued Examples 32 to 59

$$R^1(-A^1)_k(-M^1)_l(-A^2)_m(-M^2)_n(-A^3)_o(-M^3)_p-\underset{X^3}{\overset{X^1}{\underset{X^4}{\bigcirc}}}-C\equiv C-CHF_2$$

| Example No. | Structure |
|---|---|
| 46 | $H_{11}C_5$—H—⌬—$CH_2CH_2$—⌬—$C\equiv C-CHF_2$ |
| 47 | $H_{11}C_5$—H—⌬—$CH_2CH_2$—⌬(F)—$C\equiv C-CHF_2$ |
| 48 | $H_{11}C_5$—H—⌬—$CH_2CH_2$—⌬(F,F)—$C\equiv C-CHF_2$ |
| 49 | $H_7C_3$—H—⌬(F)—⌬(F)—$C\equiv C-CHF_2$ |
| 50 | $H_7C_3$—H—⌬(F)—⌬(F,F)—$C\equiv C-CHF_2$ |
| 51 | $H_{11}C_5$—H—H—⌬—$C\equiv C-CH_2CHF_2$ |
| 52 | $H_{11}C_5$—H—H—⌬(F)—$C\equiv C-CH_2CHF_2$ |
| 53 | $H_{11}C_5$—H—H—⌬(F,F)—$C\equiv C-CH_2CHF_2$ |
| 54 | $H_{11}C_5$—H—⌬—⌬—$C\equiv C-CH_2CHF_2$ |

TABLE 2-continued

Examples 32 to 59

$$R^1(-A^1)_k(-M^1)_i(-A^2)_m(-M^2)_n(-A^3)_o(-M^3)_p - \underset{X^3\ \ X^4}{\overset{X^1\ \ X^2}{\text{Ar}}} - C\equiv C - CHF_2$$

| Example No. | Structure |
|---|---|
| 55 | $H_{11}C_5$—[H]—⟨⟩—⟨F⟩—C≡C—$CH_2CHF_2$ |
| 56 | $H_{11}C_5$—[H]—⟨⟩—⟨F,F⟩—C≡C—$CH_2CHF_2$ |
| 57 | $H_{11}C_5$—[H]—⟨F⟩—⟨F⟩—C≡C—$CH_2CHF_2$ |
| 58 | $H_{11}C_5$—[H]—⟨F⟩—⟨F,F⟩—C≡C—$CH_2CHF_2$ |
| 59 | $H_{11}C_5$—[H]—⟨F,F⟩—⟨F,F⟩—C≡C—$CH_2CHF_2$ |

USE EXAMPLES

The novel substances from Examples 31 and 45 are mixed to the extent of 20% by weight with ZLI 4792 (commercially available TFT-TN mixture from E. Merck, Darmstadt). Table 1 shows how the novel substances favorably affect the physical properties of the mixture.

The novel substances are distinguished by very high anisotropy of the refractive index and of the dielectric constants, which makes them particularly suitable for STN and PDLC mixtures as well as for TFT-TN mixtures. In addition, the substances significantly lower the more highly ordered, smectic phase transition, which is advantageous. The substance from Ex. 45 has a very broad nematic phase with high clearing point and significantly extends the nematic phase range in mixtures toward high and low temperatures.

Table 2 shows that the pure substance from Ex. 31 has a low melting point and in addition, surprisingly, a nematic phase, while the undesired smectic phases are not observed. Comparative Examples 1 to 3 from WO 90/13610 exhibit, by contrast, significantly higher melting points and also have undesired smectic phases.

TABLE 1

| | 20% by weight in ZLI-4792 | | | | Extrapolated values for pure substance | |
|---|---|---|---|---|---|---|
| | | 25° C. | | | | |
| Pure substance: Structure/phases | Phase sequence/°C. | Δn | Δε | $U_{10}$ [V] | Δn | Δε |
| 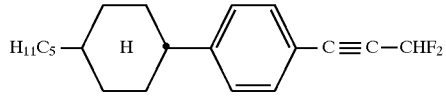 X 37 (26) N 34 I Substance from Ex. 31 | Tg − 75 (−77) $X_{re}$ − 37X − 6 $S_x$ (−50) N 80 I | 0.1031 | 5.2 | 1.97 | 0.148 | 7.8 |
| 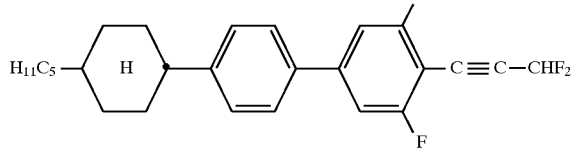 X 87 (52) N 164 I Substance from Ex. 45 | Tg − 78 (−81) X − 44$S_x$ (−56) N 105 I | 0.1235 | 6.96 | 1.85 | 0.222 | 13.7 |
| ZLI-4792 (E. Merck, Darmstadt) | Tg − 82 (−84) $X_{re}$ − 63X −31/−9$S_x$ (−44) N 94 I | 0.0955 | 5.0 | 1.94 | | |

TABLE 2

| | Structure | Phase sequence/°C. |
|---|---|---|
| Substance from Example 31 | 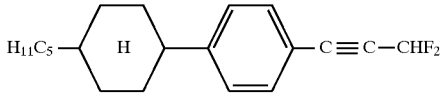 | X 37 (26) N (34) I |
| Comparative Examples from wo 90/12610 | | |
| C1 | 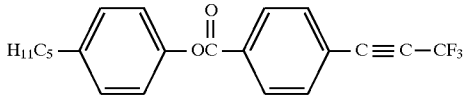 | X 63 $S_A$ (54) I |
| C2 | 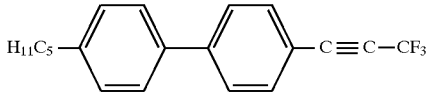 | X 108 I |
| C3 | 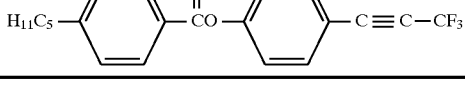 | X 77 I |

We claim:

1. A fluoroalkylethynyl- or difluoroalkylethynyl- benzene compound of the formula (I)

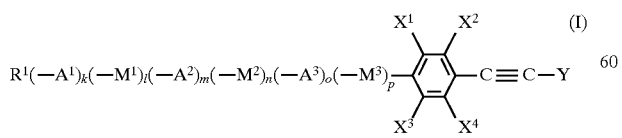

$$R^1(-A^1)_k(-M^1)_l(-A^2)_m(-M^2)_n(-A^3)_o(-M^3)_p\text{—}\underset{X^3\;X^4}{\overset{X^1\;X^2}{\text{benzene}}}\text{—}C\equiv C\text{—}Y \quad (I)$$

wherein:

$R^1$ is H, a straight-chain or branched (with or without an asymmetric carbon atom) alkyl group having 1 to 15 carbon atoms, in which one or two non-adjacent $CH_2$ groups are optionally replaced by —O—, —S—, —CO—, —CO—I—, —O—CO—, —CO—S—, —S—CO—, —O—CO—O—, —CH═CH—, —C≡C—, cyclopropane-1,2-diyl or —Si(CH₃)₂—, and in which one or more H atoms in the alkyl group are optionally replaced by F, Cl or CN;

$A^1$, $A^2$ and $A^3$ are identical or different and are 1,4-phenylene, pyrazine-2,5-diyl, pyridine-2,5-diyl or pyrimidine-2,5-diyl, in which one or two H atoms are optionally replaced by F, or trans-1,4-cyclohexylene, 1,3,4-thiadiazole-2,5-diyl, 1,3-dioxane-2,5-diyl, naphthalene-2,6-diyl, bicyclo[2.2.2]octane-1,4-diyl or 1,3-dioxoborinane-2,5-diyl;

$M^1$, $M^2$ and $M^3$ are identical or different and are each —$CH_2$—$CH_2$—, —CH=CH—, —C≡C—, —$CH_2CH_2CH_2CH_2$—, —$CH_2CH_2CH_2$—O—, —O—$CH_2CH_2CH_2$—, —$CH_2CH_2$—CO—O—, —O—CO—$CH_2CH_2$—, —$CH_2$—O—, —O—$CH_2$—, —CO—O— or —O—CO—;

k, l, m, n, o and p are zero or one, with the proviso that the sum k+m+o is greater than zero;

$X^1$, $X^2$, $X^3$ and $X^4$ are, independently of one another, H, F or Cl; and Y is —$CH_2F$ or —$CHF_2$.

2. A compound according to claim 1 wherein Y is —$CHF_2$.

3. A compound according to claim 1, wherein $X^2$ and $X^4$ are both F.

4. A compound according to claim 1, wherein:

$R^1$ is a straight-chain alkyl having 1 to 15 carbon atoms;

$A^1$, $A^2$ and $A^3$ are identical or different and are 1,4-phenylene, in which one or two H atoms are optionally replaced by F, or trans-1,4-cyclohexylene; and $X^1$, $X^2$, $X^3$ and $X^4$ are, independently of one another, H or F.

5. A compound according to claim 4, wherein Y is —$CHF_2$.

6. A process for the preparation of a compound of the formula (I) in claim 1, which comprises:

a) reacting a compound of the formula (II)

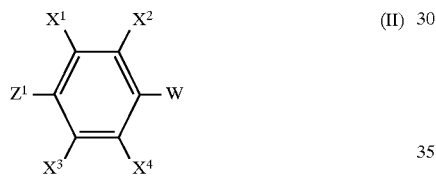

where $Z^1 = R^1(-A^1)_k(-M^1)_l(-A^2)_m(-M^2)_n(-A^3)_o(-M^3)_p$, and

W=Br, I with trimethylsilylacetylene in a cross-coupling reaction catalyzed by a palladium compound;

b) desilylating the compound from a) with a base;

c) deprotonating the compound from b);

d) reacting the compound from c) with dimethylformamide or formaldehyde, and e) fluorinating the resultant aldehyde or alcohol by reaction with diethylaminosulfur trifluoride.

7. A liquid-crystal mixture comprising one or more compounds of the formula (I) of claim 1 as liquid crystal component(s).

8. A liquid-crystal mixture according to claim 7 which exhibits nematic properties.

9. A liquid-crystal mixture according to claim 7, which comprises 1 to 8 compounds of the formula (I).

10. A liquid-crystal mixture according to claim 7, which comprises 0.1 to 70 mol % of one or more compounds of the formula (I).

11. An electro-optical switching or display device which comprises a liquid-crystal layer of a composition of claim 7.

12. The device of claim 11, which further comprises at least one alignment layer, at least one polarizer, electrodes and outer plates.

13. The device of claim 11, which is a super-twisted nematic display or thin film transistor-twisted nematic display.

14. A fluoroalkylethynyl- or difluoroalkylethynyl- benzene compound of one of the following formulae:

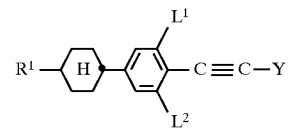

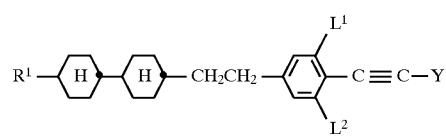

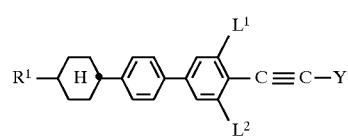

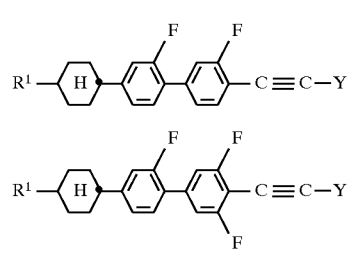

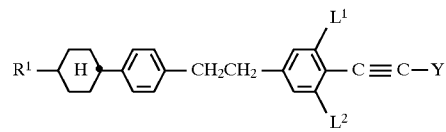

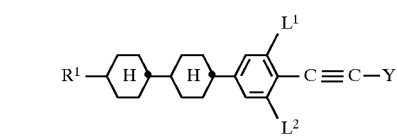

in which $R^1$ is H, a straight-chain or branched (with or without an asymmetric carbon atom) alkyl group having 1 to 15 carbon atoms, in which one or two non-adjacent $CH_2$ groups are optionally replaced by —O—, —S—, —CO—, —CO—O—, —O—CO—, —CO—S—, —S—CO—, —O—CO—O—, —CH=CH—, —C≡C—, cyclopropane-1,2-diyl or —Si($CH_3$)$_2$—, and in which one or more H atoms in the alkyl group are optionally replaced by F, Cl or CN;

Y is —$CH_2F$ or —$CHF_2$, and $L^1$ and $L^2$ are each, independently of one another, H or F.

15. A compound according to claim 14, wherein Y is —$CHF_2$.

16. A compound according to claim 14, wherein $L^1$ and $L^2$ are both F.

17. A liquid-crystal mixture comprising one or more compounds of claim 14 as liquid crystal component(s).

18. A liquid-crystal mixture according to claim 17 which exhibits nematic properties.

19. An electro-optical switching or display device which comprises a liquid-crystal layer of a composition of claim 17.

20. The device of claim 19, which further comprises at least one alignment layer, at least one polarizer, electrodes and outer plates.

21. A fluoroalkylethynyl- or difluoroalkylethynyl- benzene compound of the formula (I)

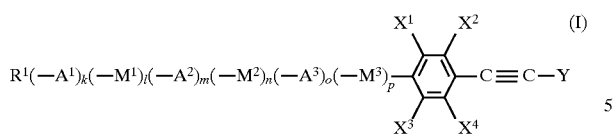
(I)

wherein:

R¹ is H, a straight-chain or branched (with or without an asymmetric carbon atom) alkyl group having 1 to 15 carbon atoms, in which one or two non-adjacent $CH_2$ groups are optionally replaced by —O—, —S—, —CO—, —CO—O—, —O—CO—, —CO—S—, —S—CO—, —O—CO—O—, —CH=CH—, —C≡C—, cyclopropane-1,2-diyl or —Si(CH₃)₂—, and in which one or more H atoms in the alkyl group are optionally replaced by F, Cl or CN;

A¹, A² and A³ are identical or different and are 1,4-phenylene, pyrazine-2,5-diyl, pyridine-2,5-diyl or pyrimidine-2,5-diyl, in which one or two H atoms are optionally replaced by F, or trans-1,4-cyclohexylene, 1,3,4-thiadiazole-2,5-diyl, 1,3-dioxane-2,5-diyl, naphthalene-2,6-diyl, bicyclo[2.2.2]octane-1,4-diyl or 1,3-dioxoborinane-2,5-diyl;

M¹, M² and M³ are identical or different and are each —$CH_2$—$CH_2$—, —CH=CH—, —C≡—C—, —$CH_2CH_2CH_2CH_2$—, —$CH_2CH_2CH_2$—O—, —O—$CH_2CH_2CH_2$—, —$CH_2CH_2$—CO—O—, —O—CO—$CH_2CH_2$—, —$CH_2$—O—, —O—$CH_2$—, —CO—O— or —O—CO—;

k, l, m, n, o and p are zero or one, with the proviso that the sum k+m+o is greater than zero;

X¹ and X³ are, independently of one another, H;

X² and X⁴ are independently of one another, F; and

Y is —$CHF_2$.

* * * * *